United States Patent [19]
Baumann et al.

[11] Patent Number: 5,786,936
[45] Date of Patent: *Jul. 28, 1998

[54] IMAGE STABILIZING DEVICE

[75] Inventors: Hans Baumann, Raisdorf; Wolfgang Graczyk, Kiel, both of Germany

[73] Assignee: Carl-Zeiss-Stiftung, Heidenheim, Germany

[*] Notice: The term of this patent shall not extend beyond the expiration date of Pat. No. 5,731,896.

[21] Appl. No.: 170,615

[22] Filed: Dec. 20, 1993

[30] Foreign Application Priority Data

Dec. 24, 1992 [DE] Germany .................. 42 44 073.4

[51] Int. Cl.⁶ .................. G02B 27/64; G02B 21/00
[52] U.S. Cl. .................. 359/557; 359/368; 359/554
[58] Field of Search .................. 359/554–557, 359/694–706, 813, 823; 310/12–19; 318/135, 685, 696; 354/403

[56] References Cited

U.S. PATENT DOCUMENTS

| | | | |
|---|---|---|---|
| 3,577,205 | 5/1971 | Hobrough | 359/557 |
| 3,756,686 | 9/1973 | Humphrey | 359/555 |
| 4,466,725 | 8/1984 | Hirohata | 354/403 |
| 4,581,553 | 4/1986 | Moczala | 310/12 |
| 4,772,841 | 9/1988 | Haruyama et al. | 318/696 |
| 4,864,339 | 9/1989 | Gross et al. | 359/363 |
| 4,952,011 | 8/1990 | Ishii et al. | 359/198 |
| 4,996,545 | 2/1991 | Enomoto et al. | 359/554 |
| 5,049,745 | 9/1991 | Vogen et al. | 250/310 |

FOREIGN PATENT DOCUMENTS 504930 3/1992 European Pat. Off. .

*Primary Examiner*—Thong Nguyen

[57] ABSTRACT

An image stabilizing device for optical equipment has at least one force exerting drive element for the compensation of vibrations acting on an optical arrangement in the optical equipment from its surroundings in at least one direction perpendicular to the optical axis. The force exerting drive elements is a linear motor. The image stabilizing device is installed in or on the optical equipment.

22 Claims, 5 Drawing Sheets

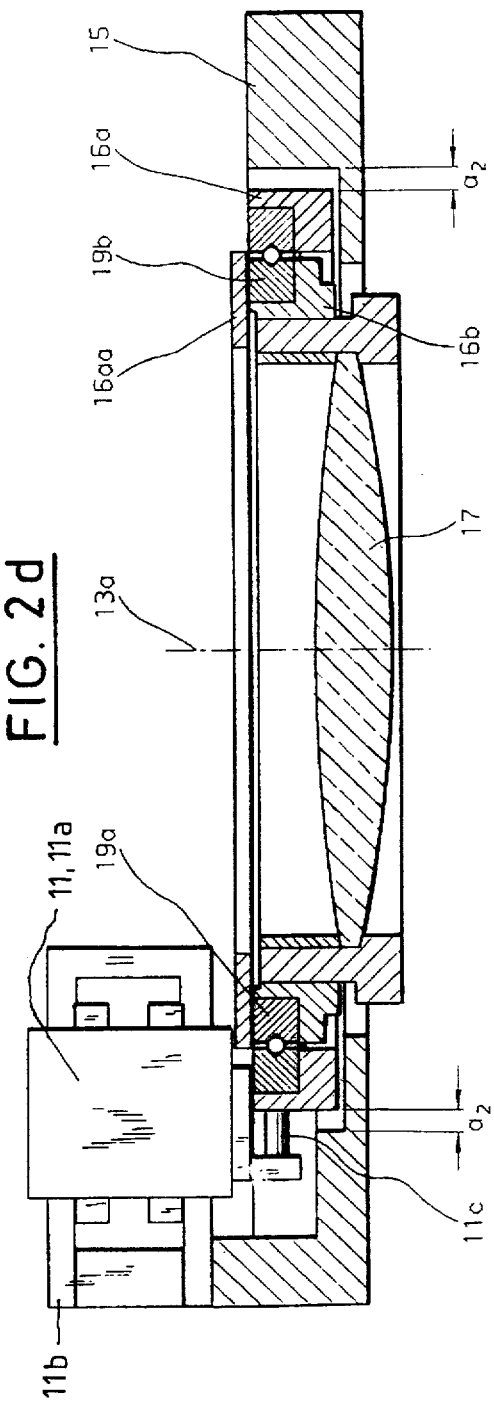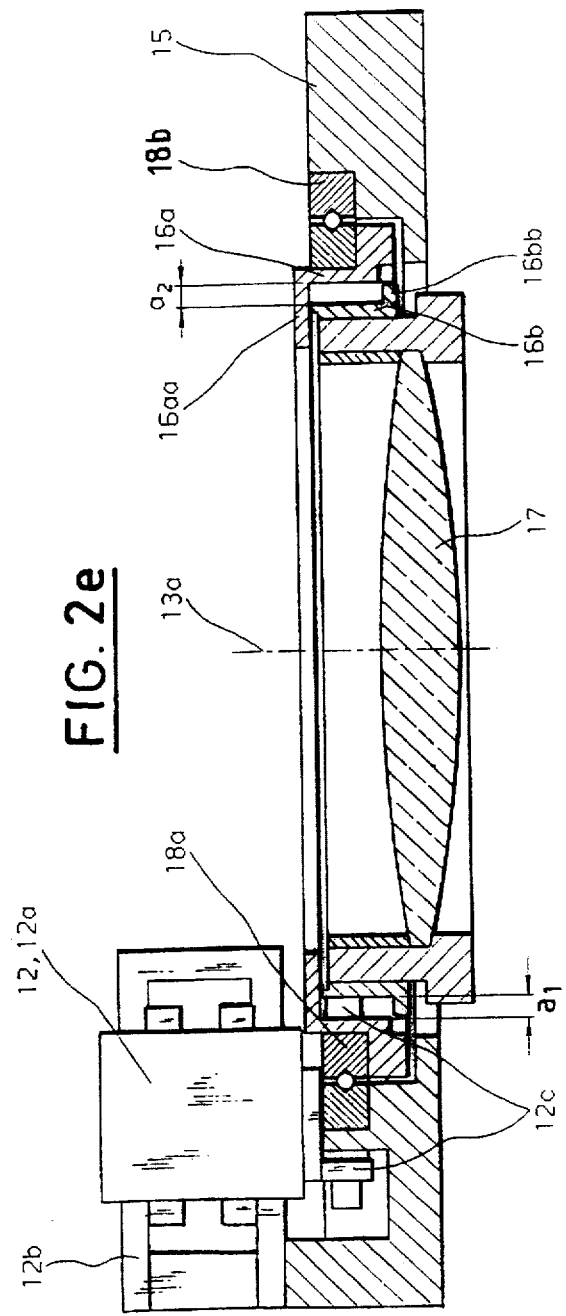

IMAGE STABILIZING DEVICE

BACKGROUND OF THE INVENTION

1. Field of the Invention

This invention relates to an image stabilizing device for optical equipment.

Optical equipment is exposed to vibrations from the surroundings. These vibrations (unintentional contact, vibrations of the building, etc.) make work difficult with this equipment, particularly when the object to be observed is not fixedly connected to the equipment.

This is particularly the case with telescopes, cameras and operation microscopes, even when these devices are mounted on stands. Operation microscopes have, in general, a magnification ≦30×. In observations with telescopes over a long period, the vibrations produced by the surroundings lead to a great reduction of the contrast and resolution, particularly during photographic exposures. The same is true for cameras. Operation microscopes are frequently fastened to a boom on the floor or on the ceiling. Since the boom has only a limited stiffness, operation microscopes, in particular, tend to oscillate when excited, so that work with this equipment is considerably hampered.

At high magnifications, the freehand use of telescopes and cameras (still or movie cameras) is barely possible, or severe blurring occurs.

2. Relevant Prior Art

Image stabilization devices are known per se. Thus, in particular, a device of this kind is known from European Patent 504,930, in which an x-y table is moved by a motor via spindles. The indirect drive via spindles has the disadvantage, that the adjustment is neither immediate nor precise. This greatly reduces the utility value of the device. In addition, the thread wears in use, so that deterioration of the accuracy of adjustment is to be expected after a time.

SUMMARY OF THE INVENTION

The object of the invention is to provide an image stabilizing device in which image movements brought about by vibration (shaking) of the optical equipment, in particular, transverse motions perpendicular to the optical axis, are suppressed as far as possible.

This object is achieved in an image stabilizing device having at least one drive element for compensating vibration acting on the optical equipment from its surroundings, a sensor for sensing the vibrations and an electronic circuit for converting signals from the sensor into signals for actuating the drive element(s), the drive element(s) being a linear motor.

Data derived from the sensor can be converted directly into a displacement motion of opposite phase by use of a linear motor, without the need for a transmission, however embodied. This leads to an extremely short reaction time because unnecessary masses do not have to be moved. In addition, the reaction is extremely precise. No gears are necessary between the motor and the portion to be displaced. Each movement of the motor leads directly to a linear motion at the portion to be displaced. No dead times and hysteresis are present. For battery-operated equipment, the high efficiency without (or with very small) frictional losses is advantageous.

BRIEF DESCRIPTION OF THE DRAWINGS

The invention is described herein below in detail by means of a preferred embodiment, with reference to the accompanying drawing. Further important features and other possibilities of embodiment will become apparent from the description of the inventive concept.

In the drawings:

FIG. 1c shows the linear motor of FIG. 1a in a front view, partially sectional along section line Ic—Ic shown in FIG. 1a;

FIG. 2b shows an objective mounting in the y-direction along section line IId—IId shown in FIG. 2b in plan view from FIG. 2a;

FIG. 2c shows an objective mounting in the x-direction in plan view from FIG. 2a;

FIG. 2d shows a sectional view through the objective mounting of FIG. 2a in the y-direction;

FIG. 2e shows a sectional view through the objective mounting of FIG. 2a in the x-direction along section IIe—IIe shown in FIG 2c;

DETAILED DESCRIPTION OF PREFERRED EMBODIMENT

Figure 1A:
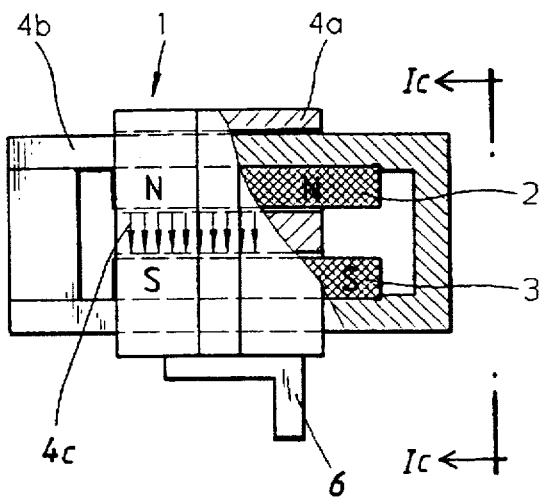
FIG. 1a shows a linear motor in partial section.
Figure 1B:
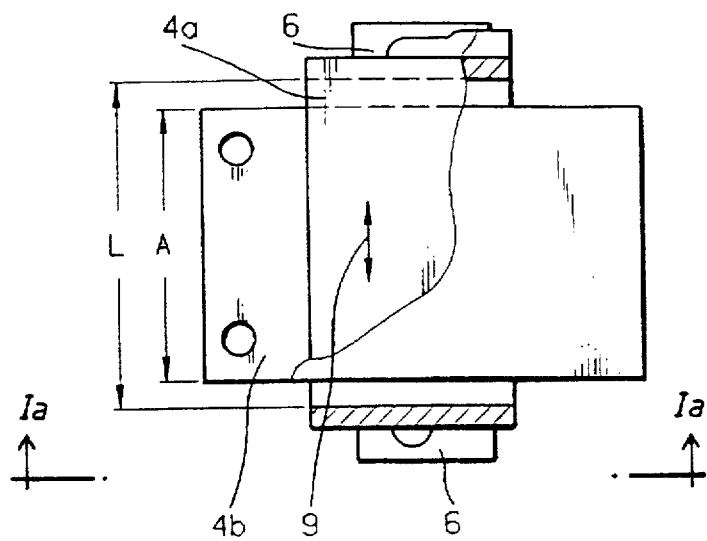
FIG. 1b shows the linear motor of FIG. 1a in plan view, partially sectional along section line Ia—Ia shown in FIG. 1b.
Figure 1C:
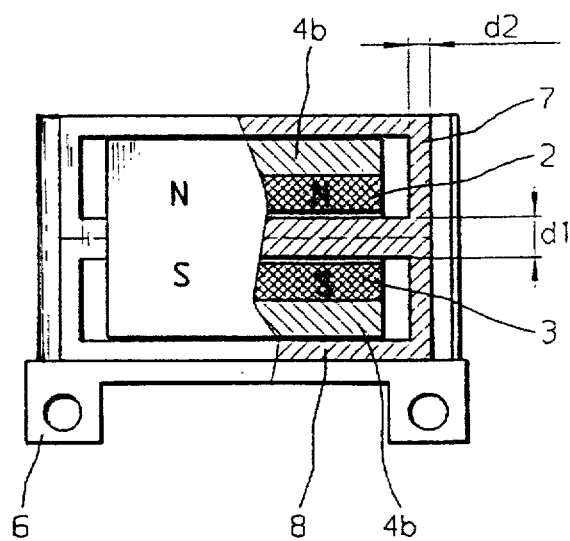
Figure 1D:
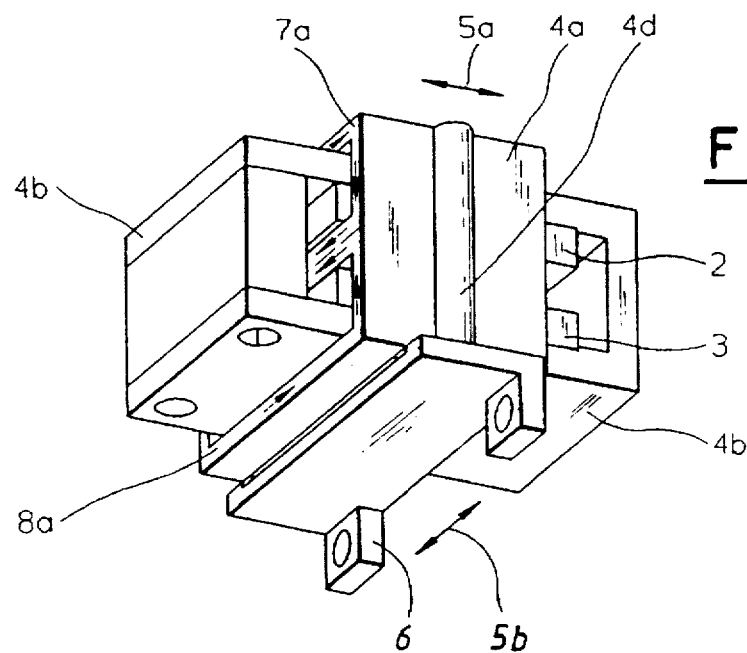
FIG. 1d shows the linear motor of FIG. 1a in perspective view.
Figure 2A:
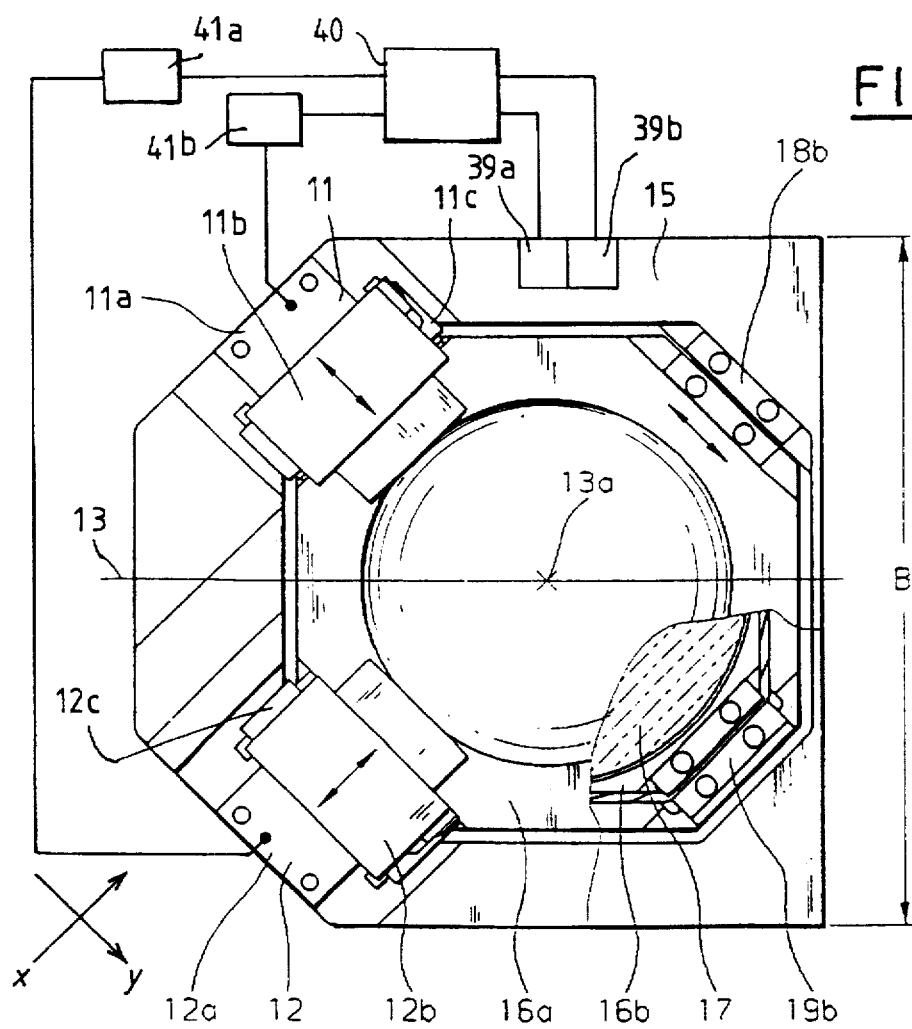
FIG. 2a shows a stabilized objective mounting in plan view, partially sectional.
Figure 2B:
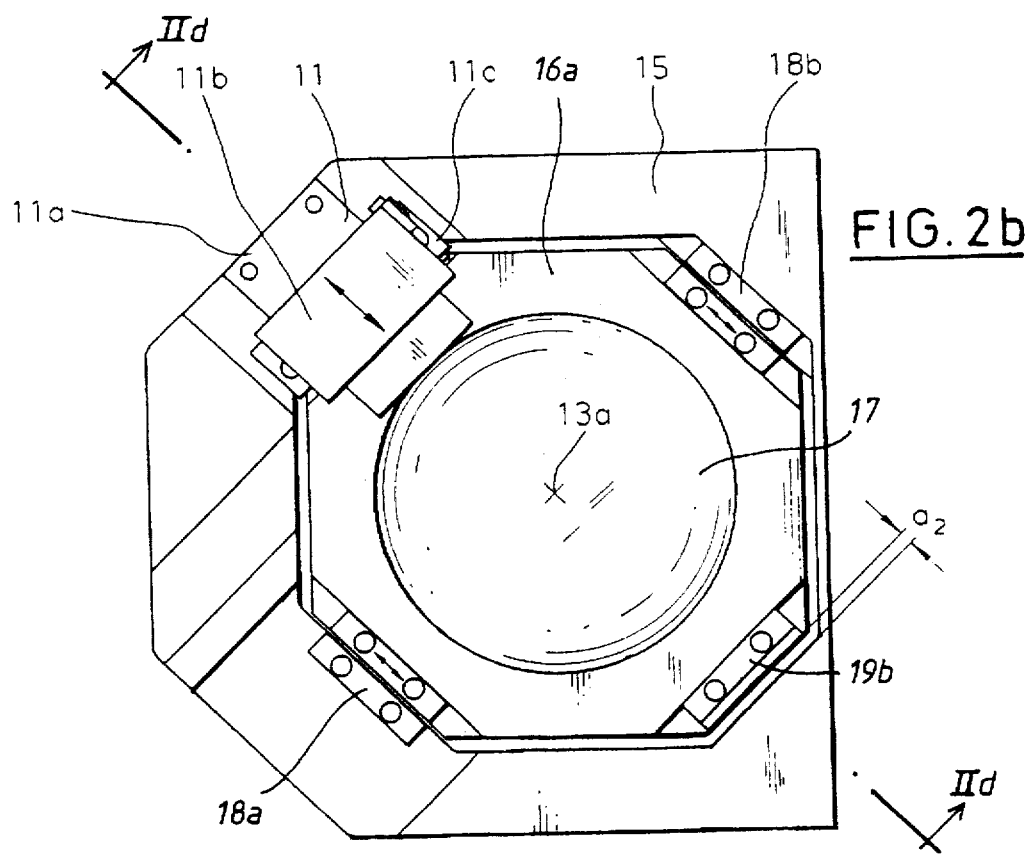
Figure 2C:
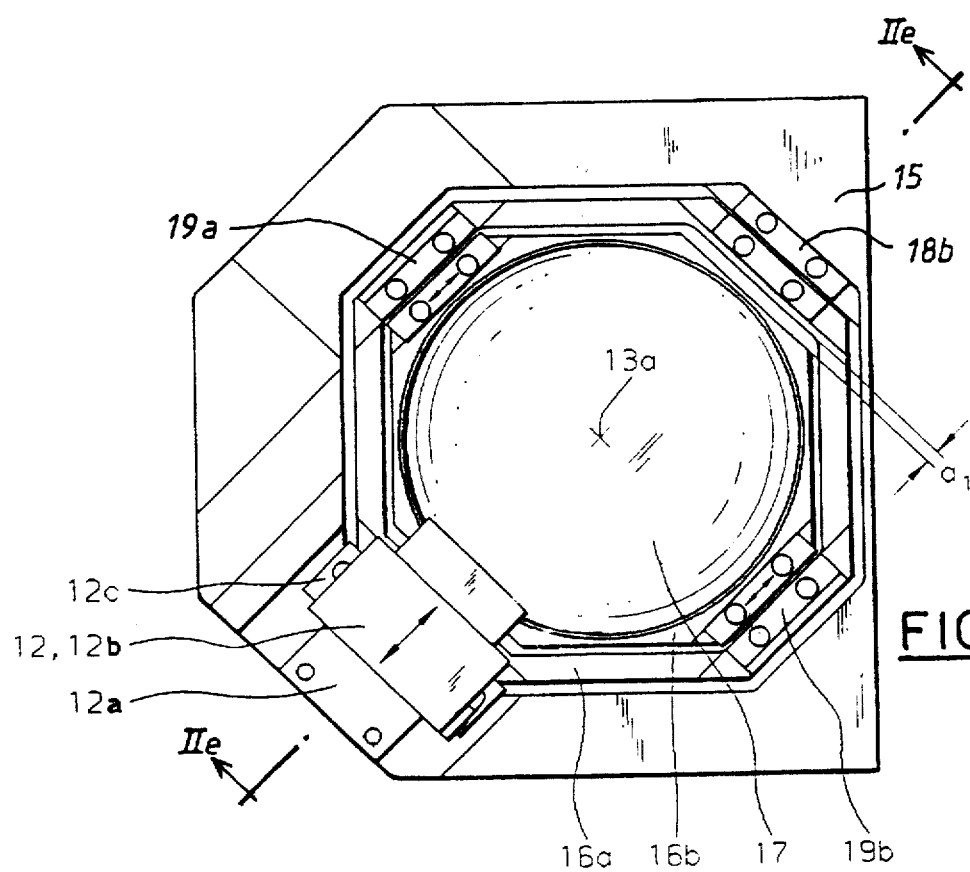

A linear motor (1) used as a drive element is shown in FIGS. 1a—d. This linear motor (1) has as essential components a coil device (4a), a stator (4b) and two permanent magnets (2, 3).

The stator (4b) is preferably a closed, U-shaped base body of a high-permeability material, such as Vacoflux. The rectangular permanent magnets (2, 3) are installed on the inner side of the two rectangularly shaped arms of the stator (4b) such that the north pole of the permanent magnet (2) is opposite the south pole of the other permanent magnet (3). A nearly homogeneous magnetic field with field lines (4c) that run perpendicularly is thereby formed between the two permanent magnets (2, 3).

The coil device (4a), also termed "rotor," is formed by a double rectangular coil, the turns of which (not drawn in the Figure) run perpendicularly to the active direction of motion (5a) of the coil device (4a) and perpendicular to the field lines (4c) of the permanent magnets (2, 3). The form of the coil device (4a) is such that one half (7a) of the coil passes over the stator (4b) and the other half (8a) of the coil passes under the stator (4b). The coil halves (7a and 8a) are cast together unsupported including the fastening device (6) (which is used to move the objective mounting, as described below). The internal width (L) of the coil device (4a) is greater than the external width (A) of the stator (4b). The coil device (4a) thereby has two degrees of freedom. On the one hand, there is a degree of freedom in the direction of motion (5a) that results from the action of the force of the magnetic field of the permanent magnets (2, 3) on the coil device (4a), through which current is flowing. On the other hand, there is a degree of freedom in a direction of motion (5b) perpendicular to the first direction of motion (5a), due to the larger internal width (L) of the coil body, without affecting the mode of action of the linear motor (1).

3

The coil device (4a) is without a core, in order to simultaneously minimize weight and volume and obtain a maximum packing density of the coil device (4a) with minimized air gaps between the rotor and the stator, especially in the field of force of the field lines (4c). This achieves the maximum possible drive forces of the linear motors (1). The coil device (4a) is a double rectangular coil from two individual rectangular coils (7, 8), the turns being divided half between each individual coil.

To produce the coil device (4a), each of the two rectangular coils (7, 8) is wound on a suitable mandrel with the required cross section. Thereafter, the coils (7, 8), including the fastening device (6), are assembled into a mold and cast together. The coil device (4a) thus obtained has an optimum mechanical strength and thermal conductivity, with maximum packing density and minimized construction volume.

The effective surface for carrying heat away is increased by 60% in this double coil body (4a) in comparison with a single rectangular coil, in which the turns are not divided.

A further increase in the liberation of heat is achieved by profiling (4d) on the coil body (4a), produced in a casting mold.

The coil body (4a) has different coil thicknesses, (d1, d2), wherein d2=d1/2.

By the division of the turns (7a, 8a) that encircle the stator (4b) the coil width is reduced by d1=2×d2.

A further increase in the relationship of power to volume is achieved by the use of coil wire with a square cross section.

The turns (7a, 8a) in the coil device do not run exactly perpendicular to the limiting direction (5a) because of the required forward feed during winding. The transverse component that thereby arises, can be largely compensated in the double coil body, in that the two coil halves are wound with a different sense of winding and subsequently cast. The transverse component of the one half then largely cancels the transverse component due to the inclined lay of the turns in the other half in the opposite direction.

The installation of two linear motors (11, 12) shown in FIGS. 1a–1d and the objective mounting is described in FIGS. 2a–2e.

To minimize space requirements, the motors (11,12) are arranged offset at a 45° angle to the mid plane (13) of an adapter. The adapter width (B) can thereby be kept to a minimum. The stator (11a, 12a) is fixedly connected to a base-plate (15) of the adapter. The double coil (11b) is connected via a fastening device (11c) to an intermediate ring (16a), which is designed as a table guide in the y-direction. As against this, the double coil (12b) is connected by means of the fastening device (12c) through the intermediate ring (16a) to an objective holder designed as a table guide in the x-direction.

An objective (17) is received by the octagonal objective holder (16b), which is in an inner location and permits a motion of the objective (17) in the x-direction. The optical axis (13a) of the objective (17) is located exactly in the center of the objective holder (16b) into which the objective (17) is screwed. The objective holder (16b) is connected to the intermediate ring (16a), for as little friction as possible, by means of two linear guide pairs (19a, 19b). Motion of the inner objective holder (16b) relative to the intermediate ring is only possible in one direction, i.e., the x-direction.

The objective holder (16b) has a free space ($a_1$) in the x-direction that is available for motion of the objective within the intermediate ring (16a). In the y-direction, which

4 is perpendicular to the x-direction, the intermediate ring (16b), together with the linear guide parts (18a, 18b) installed on it, has a free space ($a_2$), that is available for motion of the objective (17) in the y-direction.

The mutually opposed linear guide pairs (18a, 18b) of the intermediate ring (16a) are arranged offset by 90° with respect to the two opposed linear guide pairs (19a, 19b) of the objective holder (16b), and are fixedly connected to the housing (15) of the adapter. The linear guide pairs (18a, 18b and 19a, 19b, respectively) are designed such that the objective (17) can move easily in both the x-direction and y-direction.

An x/y table guide system is described herein above, and permits motion of the objective (17) diagonally to the outer limits of the housing (15) in these two directions. This x/y table guide system has a high stiffness with minimum construction masses, with the center remaining free in order not to intersect the optical beam path through the objective (17) in the z-direction.

The resulting interleaved type of construction is shown in FIGS. 2d and 2e. Here in particular the inward-drawn collar (16aa) of the outer intermediate ring (16a) contributes to increasing the stiffness, without increasing the construction size. This collar (16aa) can be modified in its geometry and optimized according to the conditions for its incorporations. The same holds for the construction form of the inner objective ring (16b) and for the reinforcing collar (16bb) located on it.

The components of the mechanical vibrations are measured by two acceleration sensors (39a, 39b) arranged perpendicularly to each other. The related path components are computed from the acceleration values by a double integration. The values thus obtained represent the reference values for a PID (Proportional, Integral, Differential) controller. The controller (40) controls two final power stages (41a, 41b) that are associated with the components and which drive the two linear motors (11, 12).

The linear motors (11, 12) move the objective (17) mounted in an x/y table in opposite phase to the vibration motion. The actual value at any instant is sensed by linear path sensors associated with the components and is fed to the controller as the correction variable.

The opposite-phase deflection of the main objective (17) or of optically imaging portions greatly reduces the deterioration of the image due to the vibration of the whole microscope. This deterioration is otherwise subjectively perceived even in the magnification range ≦30× with an ideally adjusted microscope. The observer's eye in the exit pupil of the microscope can no longer follow the image motions enlarged by the magnification factor, so that the image quality is subjectively perceived as very bad. In contrast to this, a relative motion of the main objective (17) indeed leads objectively to a slightly worse image quality, but subjectively to an essentially better image, considered as a whole. The image motion is so greatly reduced that the eye can again follow the structural details, and an image is only then perceived. With a stationary microscope, i.e. not subjected to vibrations, the objective is adjusted in the optical axis (13a), and the same image quality is achieved as with a normal microscope.

The embodiment described in FIGS. 2a–2e ensures that solely in the case of vibrating microscopes, i.e., at a measured acceleration value within a plane perpendicular to the optical axis of the objective, does a response (i.e., a contrary motion) take place.

This means that in the case of approximately constant translational motions with negligible acceleration values, no motion compensation takes place, because the eye can follow the change of the image. On the other hand, in the case of inadvertent vibrations with corresponding acceleration values, for example in the higher magnification range, an image is in fact subjectively perceived due to the motion compensation which is brought into action.

Figure 3A:
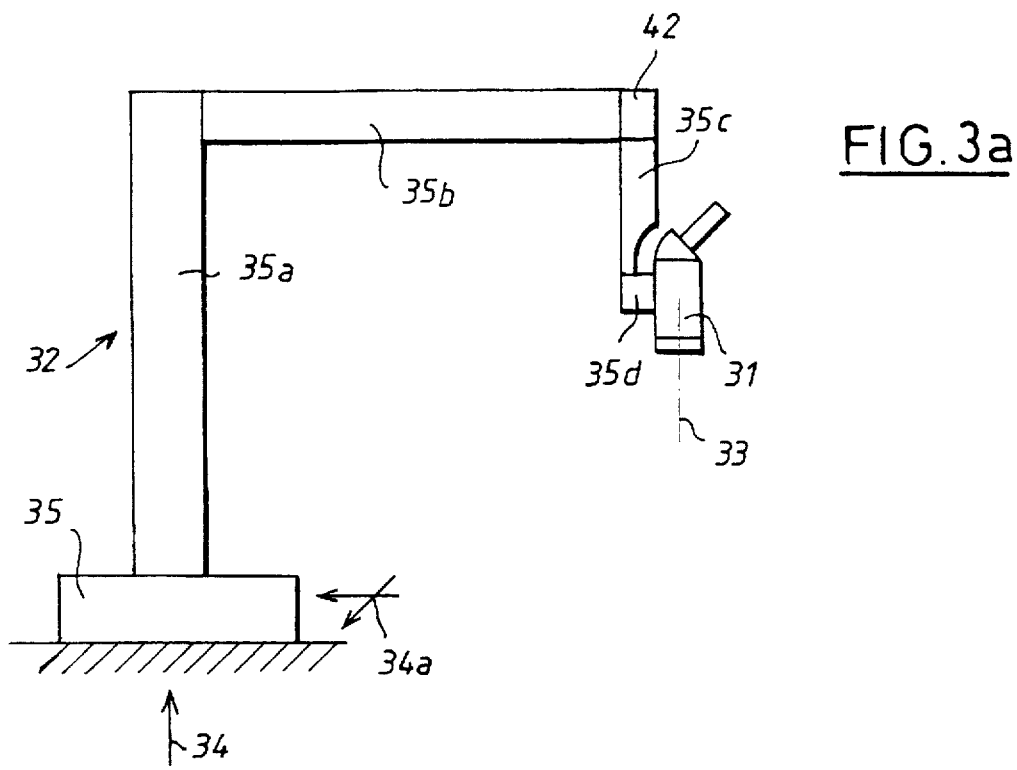
FIG. 3a shows an operation microscope on a stand.
Figure 3B:
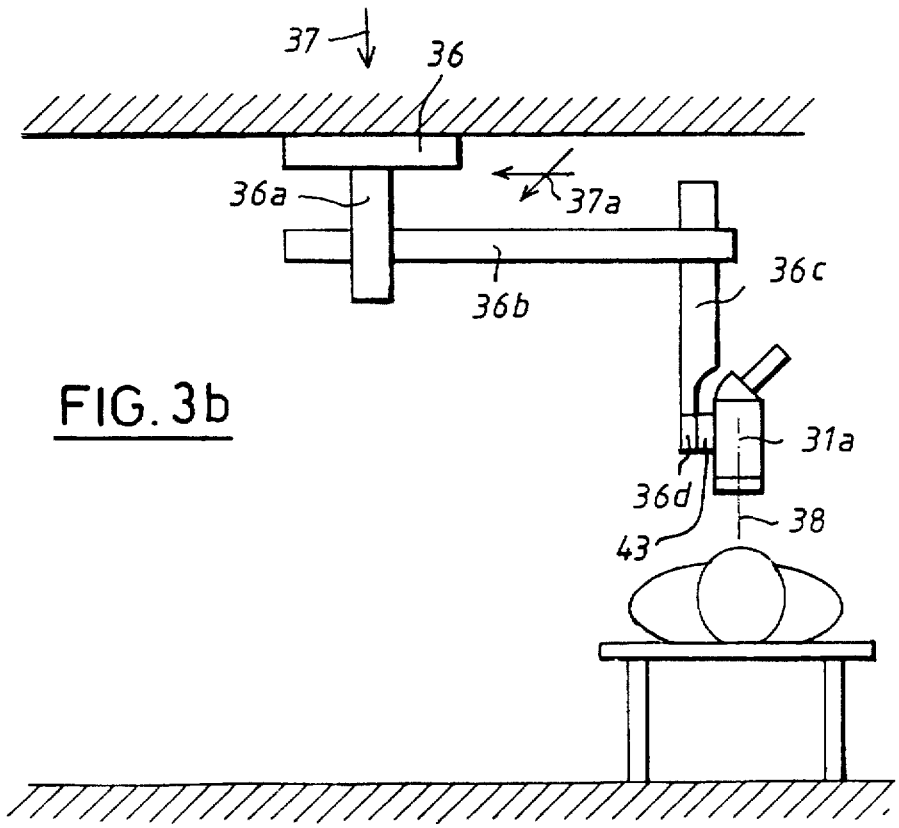
FIG. 3b shows an operation microscope on a ceiling suspension.

An operation microscope (31, 31a) in conventional suspensions, as are usual in the operating theater, is shown in FIGS. 3a and 3b.

If the operation microscope (31) is fastened to a stand (32), both axial (34) and transverse (34a) forces act on the stand foot (35). These forces (34, 34a) then lead to a corresponding motion of the operation microscope (31), because the forces (34, 34a) are transmitted by components (35a, 35b, 35c, 35d) of the stand (32).

Even when the operation microscope (31a) is fastened to the ceiling of an operating theater with a ceiling suspension, the axial and transverse forces (37, 37a) are transmitted to the operation microscope (31a) by a ceiling anchoring (36) and components (36a, 36b, 36c, 36d) of the ceiling suspension (36).

A decoupling of the operation microscope (31, 31a) can now take place a) with a force exerting device (42) between the vertical load-bearing column (35c, 36c) and the horizontal load-bearing bracket (35b, 36b);

b) with a force exerting device (43) between the vertical load-bearing column (35c, 36c) and the operation microscope (31, 31a);

c) with a force exerting device in the operation microscope (31, 31a).

In the examples in FIGS. 2a–2e, decoupling in the operation microscope (31, 31a) is carried out with respect to transverse vibrations, because definition of the image of the operation microscope (31, 31a) normally makes it unnecessary to eliminate the axial vibrations in the optical axis of the operation microscope (31, 31a). If these axial vibrations are also to be eliminated, this can be accomplished by known automatic focusing devices.

The particular advantage of eliminating the transverse vibrations in the operation microscope (31, 31a) is that the masses to be moved are very small. The compensating device therefore can be very compact and can be designed as an adapter. This advantage is supplemented by a rapid reaction time of the system.

An advantage of the invention is that linear motors require a relatively small geometric volume. Thus, the whole stabilizing device can be kept very small. It is also advantageous that the linear motor is constructed from a coil device with many turns, a stator, and two permanent magnets. A particularly small, compact linear motor is thereby obtained. The stator has a preferably closed, U-shaped base body. This furthers the compactness of the linear motor, by optimizing the magnetic flux. Further compactness is obtained because the two permanent magnets are fitted to two arms of the stator, the north pole of one permanent magnet being opposite the south pole of the other permanent magnet. The coil device is a double rectangular coil, and compactness of the linear motor is furthered.

The inner width of the coil device is greater than the outer width of the stator. Thus, controlled linear motion in one direction is possible. Additionally, motion in the direction perpendicular to this direction can be superimposed. Frequently, this is required in vibration compensation because normally there is no preferred direction.

The coil device has no core, and the linear motor can be constructed more compactly. The coil device is profiled, so that the linear motor is more able to give up heat, and its thermal stability and power reserve are improved. The coil wire of the turns of the coil device has a rectangular cross section. The turns require less space and the linear motor can be constructed more compactly.

The force exerting device of the image stabilizing device includes at least two linear motors as driving means, which are arranged in a plane perpendicular to the optical axis at an angle of 90° to each other. An image stabilization is possible in the two axes perpendicular to the optical axis.

Further space reduction is achieved because two mutually opposed linear motors are used for each degree of freedom of movement. The force required to move the movable optical components is then divided between two motors, which with a rotationally symmetrical arrangement contributes to further reduction for construction volume.

The image stabilization can also be used on already existing optical equipment. A linear motor acting as the driving means is fixed to an adapter.

Aligning the drive direction of the linear motor in a direction perpendicular to the optical axis avoids the need for a gear between the motor and the apparatus to be moved. This leads to a compact and, in particular, a direct acting arrangement, in which friction losses between the linear motor and the apparatus to be moved are small. Friction losses are also reduced when the coupling between the linear motor and the driven part is fixed.

An optical component of the optical equipment (objective, image reversal system, ocular, and the like) is decoupled by at least one linear motor in the image stabilizing device, with respect to the other optical components and the equipment housing. Thereby the number of the optical components is not increased by the image stabilization. This is particularly advantageous for telescopes because each additional optical component leads to undesired losses of light. This can take place in an advantageous manner in that the objective is decoupled by at least one linear motor with respect to the equipment housing of the ocular. When the objective is decoupled in two degrees of freedom perpendicular to the optical axis, the most troublesome effects due to vibrations acting from the surroundings (the environment) can be eliminated. When the photo device in a telescope is considered as part of the optical system, this component can also be decoupled as described.

When the force exerting device is within the optical equipment, the optical equipment can be kept very compact. An image stabilizing device of the following design leads to a very compact arrangement: an objective mounting is movable relative to the housing in at least one direction perpendicular to the optical axis, and one portion of the driving means is fixedly connected to the housing, and a second portion is connected to the objective mounting. An embodiment that is very stable mechanically is obtained by an image stabilizing device in which the objective mounting essentially consists of two mountings (x-mounting and y-mounting) that do not interfere with each other in their motions with the x- and y-axis being oriented perpendicular to each other and perpendicular to the optical axis. The mountings have a sufficiently free optical opening around the optical axis so that the optical beam can go through the image stabilizing device while the external dimensions remain small. A mechanically very stable image stabilizing device is obtained because each mounting has two mutually opposed liner guides that are offset by 90° as far as possible. The stability of the image stabilizing device is conveniently obtained when at least one main objective lens is fastened in an objective mounting and the driving means effects a displacement of the objective mounting in the opposite phase to the vibration. The sensor for sensing the vibrations is an acceleration sensor.

We claim:

1. Image stabilizing device for optical equipment including an optical arrangement comprising:
    at least one driving means for compensating vibrations acting on said optical arrangement from its surroundings,
    a sensor for sensing and providing signals in respect to said vibrations,
    an electronic circuit for converting signals from said sensor into signals for actuating said driving means, wherein
        said driving means comprises a linear motor,
        said linear motor comprises a coil device having a substantial plurality of turns, a stator, and two permanent magnets, and
        said stator comprises a closed unshaped body.

2. Image stabilizing device according to claim 1, wherein said stator has two arms and said two permanent magnets are respectively attached to said two arms of said stator, the north pole of one permanent magnet being located opposite the south pole of the other permanent magnet.

3. Image stabilizing device according to claim 1, wherein said coil device comprises a double rectangular coil.

4. Image stabilizing device according to claim 1, wherein said coil device is coreless.

5. Image stabilizing device according to claim 1, wherein said coil device has a profiling.

6. Image stabilizing device according to claim 1, wherein said turns of said coil device are comprised of coil wire having a rectangular cross section.

7. Image stabilizing device according to claim 1, wherein said optical arrangement has an optical axis, further comprising at least two driving means arranged at an angle of approximately 90° relative to each other in a plane perpendicular to said optical axis.

8. Image stabilizing device according to claim 1, further comprising an adapter on which said driving means is arranged.

9. Image stabilizing device according to claim 1, wherein said optical arrangement has an optical axis, and said linear motor has a drive direction that is aligned perpendicular to said optical axis.

10. Image stabilizing device according to claim 1, further comprising a driven portion fixedly coupled to said linear motor.

11. Image stabilizing device according to claim 1, wherein said optical arrangement comprises a first optical component that is decoupled by said linear motor with respect to other optical components of said optical arrangement.

12. Image stabilizing device according to claim 11, wherein said optical equipment includes a housing that is decoupled by said linear motor from said first optical component.

13. Image stabilizing device according to claim 12, wherein said optical arrangement includes an ocular and said optical component comprises an objective that is decoupled by said linear motor with respect to said housing and said ocular.

14. Image stabilizing device according to claim 1, wherein said optical arrangement has an optical axis and includes an objective that is decoupled by said driving means in two degrees of freedom perpendicular to said axis.

15. Image stabilizing device according to claim 1, wherein said driving means is located within said optical element.

16. Image stabilizing device according to claim 15, wherein said optical arrangement has an optical axis, and said optical equipment includes a housing, further comprising an objective mounting that is movable relative to said housing in at least one direction perpendicular to said optical axis, wherein said driving means includes a first portion fixedly connected to said housing and a second portion fixedly connected to said objective mounting.

17. Image stabilizing device according to claim 16, wherein said objective mounting comprises two movable mountings oriented along an x-axis and a y-axis respectively, said x-axis and said y-axis being oriented perpendicular to each other and to said optical axis, said two movable mountings being arranged such that they do not interfere with each other in their motions.

18. Image stabilizing device according to claim 17, wherein each of said two movable mountings has a sufficiently free optical opening extending from said optical axis to enable an optical beam to pass through said image stabilizing device.

19. Image stabilizing device according to claim 17, wherein each of said two movable mountings has two mutually opposite linear guides, the two linear guides of one mounting being arranged offset by 90° relative to the two linear guides of the other mounting.

20. Image stabilizing device according to claim 1, further comprising an objective mounting and at least one main objective lens fastened in said objective mounting, said driving means effecting a displacement of said objective mounting opposite in phase to said vibrations.

21. Image stabilizing device according to claim 1, wherein said sensor for sensing vibrations comprises an acceleration sensor.

22. Image stabilizing device for optical equipment including an optical arrangement comprising:
    at least one driving means for compensating vibrations acting on said optical arrangement from its surroundings,
    a sensor for sensing and providing signals in respect to said vibrations,
    an electronic circuit for converting signals from said sensor into signals for actuating said driving means, wherein
        said driving means comprises a linear motor,
        said linear motor comprises a coil device having a substantial plurality of turns, a stator, and two permanent magnets, and
        said stator has an external width (A) and said coil device has an internal width (L) that is greater than said external width (A) of said stator.

* * * * *